United States Patent [19]
Overton et al.

[11] Patent Number: 5,817,060
[45] Date of Patent: *Oct. 6, 1998

[54] UNIDIRECTIONAL BLUNTING APPARATUS FOR HYPODERMIC NEEDLES

[75] Inventors: Richard A. Overton, Santa Ana; Charles W. Dickerson, Tustin; Ronald B. Luther, Newport Beach, all of Calif.

[73] Assignee: Luther Medical Products, Inc., Tustin, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 614,809

[22] Filed: Mar. 8, 1996

[51] Int. Cl.$^6$ .................................................. A61M 5/178
[52] U.S. Cl. ............................................................ 604/164
[58] Field of Search ................................... 604/164, 165, 604/168, 162, 158, 170, 171

[56] References Cited

U.S. PATENT DOCUMENTS

| | | | |
|---|---|---|---|
| 2,623,520 | 12/1952 | Bamford, Jr. | 128/221 |
| 2,623,521 | 12/1952 | Shaw | 128/221 |
| 2,847,995 | 8/1958 | Adams | 128/214 |
| 3,344,786 | 10/1967 | Berg et al. | 128/215 |
| 3,463,152 | 8/1969 | Sorenson | 128/214.4 |
| 3,491,756 | 1/1970 | Bentov | 128/221 |
| 3,536,073 | 10/1970 | Farb | 128/214.4 |
| 3,809,081 | 5/1974 | Loveless | 128/214.4 |
| 3,923,066 | 12/1975 | Francisoud et al. | 128/348 |
| 4,233,975 | 11/1980 | Yerman | 128/218 P |
| 4,274,408 | 6/1981 | Nimrod | 128/214.4 |
| 4,417,886 | 11/1983 | Frankhouser | 604/53 |
| 4,509,945 | 4/1985 | Kramann et al. | 604/164 |
| 4,525,157 | 6/1985 | Vaillancourt | 604/52 |
| 4,529,399 | 7/1985 | Groshong et al. | 604/53 |
| 4,631,057 | 12/1986 | Mitchell | 604/198 |
| 4,652,256 | 3/1987 | Vaillancourt | 604/52 |
| 4,664,654 | 5/1987 | Strauss | 604/198 |
| 4,676,783 | 6/1987 | Jagger et al. | 604/171 |
| 4,702,738 | 10/1987 | Spencer | 604/198 |
| 4,731,068 | 3/1988 | Hesse | 604/110 |
| 4,747,831 | 5/1988 | Kulli | 604/110 |
| 4,762,516 | 8/1988 | Luther et al. | 604/164 |
| 4,772,264 | 9/1988 | Cragg | 604/158 |
| 4,778,453 | 10/1988 | Lopez | 604/110 |
| 4,781,692 | 11/1988 | Jagger et al. | 604/164 |
| 4,826,490 | 5/1989 | Byrne et al. | 604/198 |
| 4,828,547 | 5/1989 | Sahi et al. | 604/110 |
| 4,828,549 | 5/1989 | Kvalo | 604/164 |
| 4,832,693 | 5/1989 | Gloyer | 604/110 |
| 4,832,696 | 5/1989 | Luther et al. | 604/164 |
| 4,834,718 | 5/1989 | McDonald | 604/195 |
| 4,863,431 | 9/1989 | Vaillancourt | 604/168 |
| 4,869,717 | 9/1989 | Adair | 604/51 |
| 4,917,671 | 4/1990 | Chang | 604/168 |
| 4,944,728 | 7/1990 | Carrell | 604/164 |
| 4,950,252 | 8/1990 | Luther et al. | 604/198 |
| 5,009,642 | 4/1991 | Sahi | 604/158 |
| 5,104,381 | 4/1992 | Gresl | 604/164 |
| 5,147,316 | 9/1992 | Castillenti | 604/164 |
| 5,190,050 | 3/1993 | Nitzsche | 604/164 |
| B1 4,417,886 | 1/1991 | Frankhouser | 604/53 |

Primary Examiner—Manuel Mendez
Attorney, Agent, or Firm—Stetina Brunda Garred & Brucker

[57] ABSTRACT

An apparatus which is useable to blunt the sharpened distal tip of a hypodermic needle, said apparatus comprising an elongate blunting member which is axially disposable within the lumen of the needle, and which is axially advanceable from a "non-blunting" position within the lumen to a "blunting" position wherein the blunt distal tip of the blunting apparatus protrudes out of the distal end of the needle. A positioning member may be formed on the proximal end of the blunting apparatus, said positioning member being engageable with the needle to alternately hold the blunting member in either its "non-blunting" position or its "blunting" position. One such positioning member comprises a generally cylindrical body having a series of elastomeric engagement fins formed thereon such that, when advanced into the hollow bore of the needle hub, the engagement fins will be proximally deflected and frictionally engaged thereby. Such proximal deflection and frictional engagement of the engagement fins deters proximal extraction of the blunting member, but allows the blunting member to be further advanced in the distal direction.

5 Claims, 2 Drawing Sheets

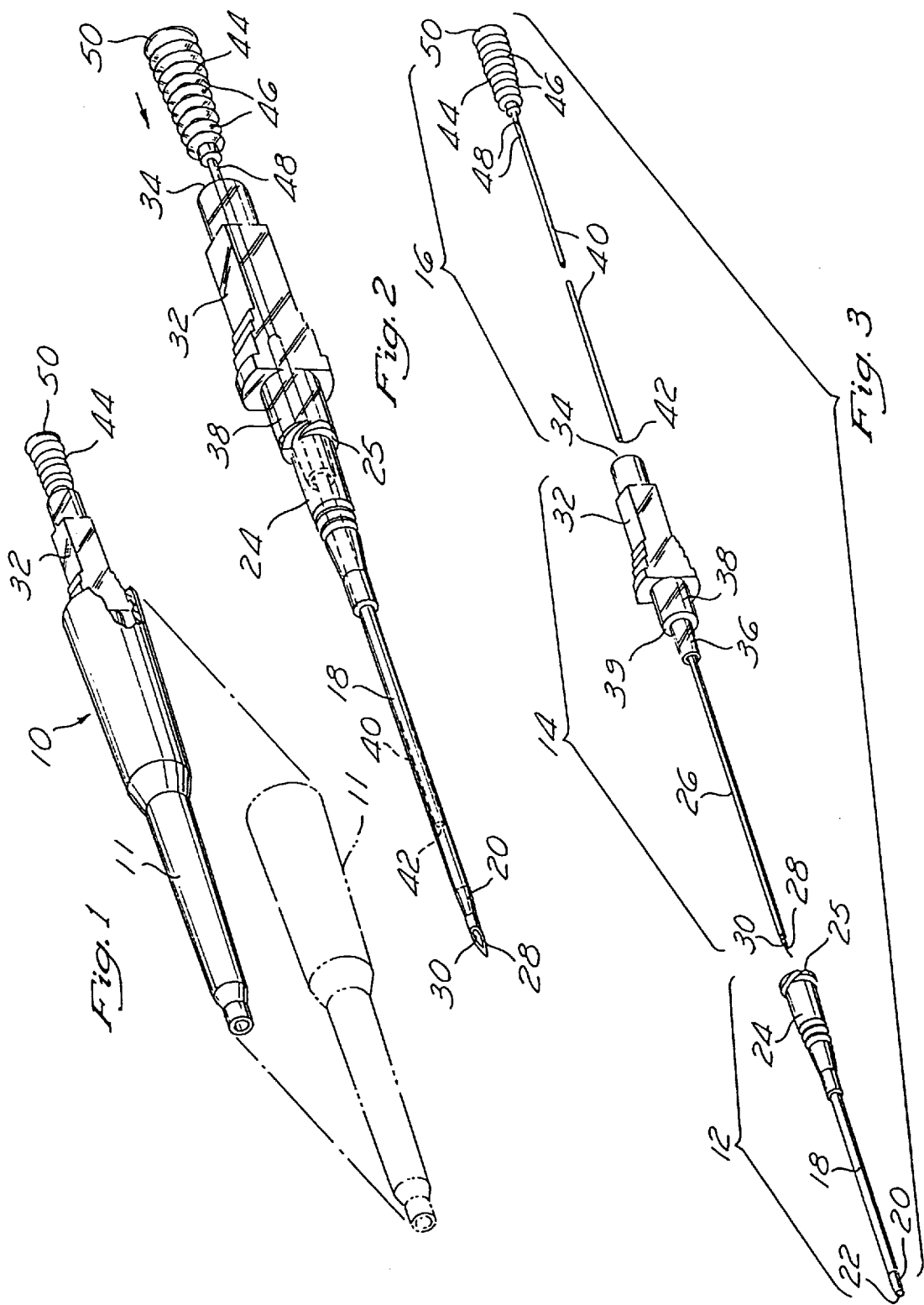

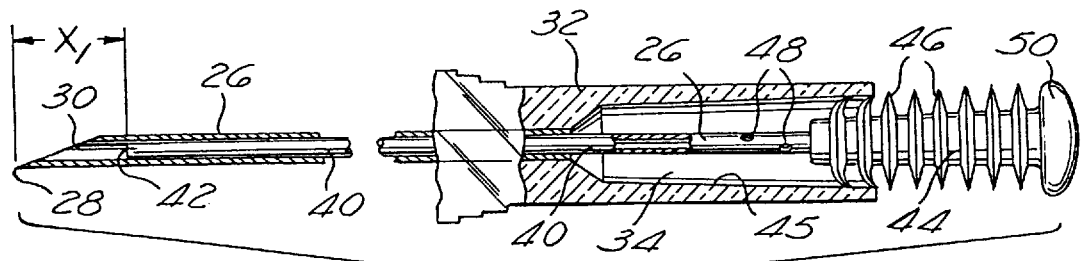
Fig. 4
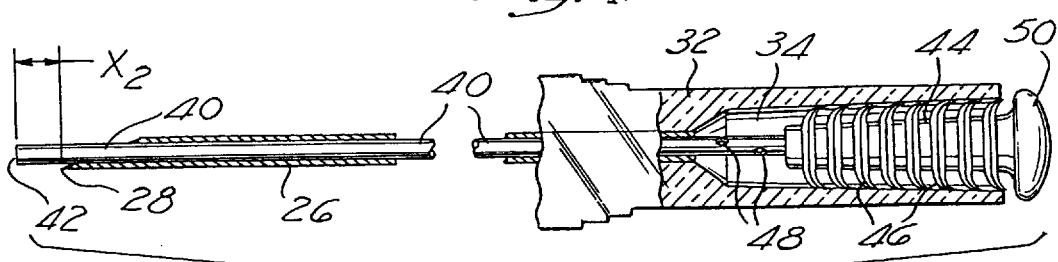
Fig. 5
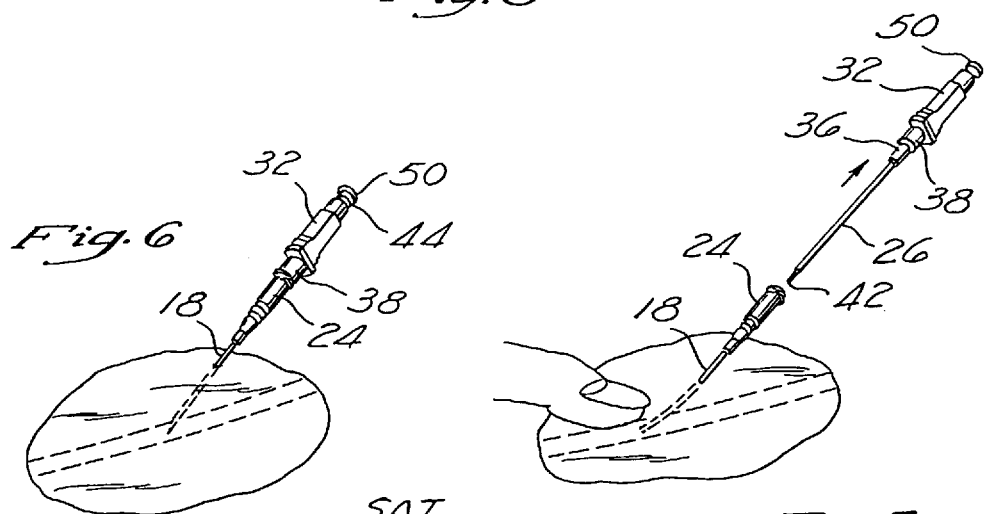
Fig. 6
Fig. 7
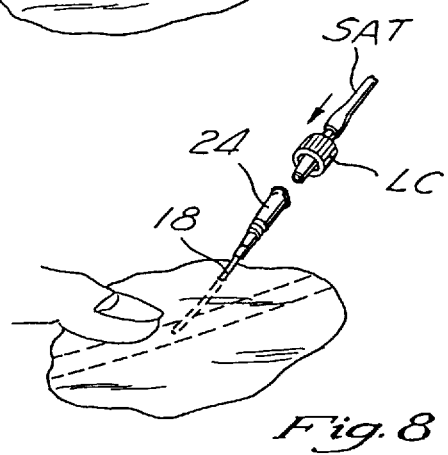
Fig. 8

UNIDIRECTIONAL BLUNTING APPARATUS FOR HYPODERMIC NEEDLES

FIELD OF THE INVENTION

The present invention relates generally to medical devices, and more particularly to a blunting apparatus useable to prevent hypodermic needles from causing inadvertent penetration trauma.

BACKGROUND OF THE INVENTION

In view of the potential for inadvertent infection of healthcare workers with blood born pathogens such as human immunodeficiency virus (HIV) and hepatitis B. There exists an ongoing motivation to provide safety devices and apparatus for preventing healthcare workers from incurring inadvertent needle trauma when handling used hypodermic needles.

Examples of devices and apparatus which have heretofore been known for preventing inadvertent trauma by hypodermic needles (e.g., intravenous needles) and the like, include those described in U.S. Pat. Nos. 5,112,312; 5,120,317 and 5,273,540.

Although many of the heretofore proposed needle safety devices and apparatus do effectively prevent or deter inadvertent needle trauma, none of these prior devices or apparatus are universally usable in connection with all types of hypodermic needles, in all applicable clinical situations. Accordingly, there remains a need for the development of additional safety devices and/or apparatus for preventing or deterring inadvertent needle sticks, especially when handling used hypodermic needles.

SUMMARY OF THE INVENTION

The present invention provides a blunting apparatus which is usable in conjunction with any type of hollow needle having a sharpened distal tip. The blunting apparatus preferably comprises an elongate blunting member having a blunt distal tip, and an outer diameter which is only slightly smaller than the inner diameter of the needle lumen. The blunting member is axially disposed within the needle lumen and is moveable from first "non-blunting" position wherein the blunt distal tip of the blunting member resides within the lumen of the needle, to a second "blunting" position wherein the blunt distal tip of the blunting member protrudes out of the sharpened distal tip of the needle. A positioning member may be formed on the proximal end of the blunting member, such positioning member being engageable with the proximal end of the needle to alternately hold the blunting member in its "non-blunting" or its "blunting" position.

In accordance with the invention, one type of positioning member which may be mounted on the proximal end of the blunting member is a generally cylindrical member having a series of annular engagement fins formed thereabout. Such annular engagement fins are preferably formed of elastomeric or pliable material, and are sized to be advanceable into the bore of a proximal hub formed on the hollow needle. In this regard, as the engagement fins are advanced into the bore, they will be proximally deflected by and frictionally engaged by the inner surface of the needle hub bore. In this manner, such proximal deflection and frictional engagement of the annular fins with the inner surface of the needle hub bore will substantially hold the blunting member in either its "non-blunting" or its "blunting" position, and will substantially deter inadvertent proximal retraction of the blunting member.

Various additional objects and advantages of the present invention will become apparent to those skilled in the art upon reading and understanding of the following detailed description of a preferred embodiment.

BRIEF DESCRIPTION OF THE DRAWINGS

FIG. 1 is a perspective view of an over-the-needle intravenous cannula assembly of the present invention having a needle safety sheath mounted thereon.

FIG. 2 is a perspective view of the intravenous cannula assembly of FIG. 1 following removal of the needle safety sheath therefrom and following slight proximal retraction of the needle blunting apparatus which is incorporated therein.

FIG. 3 is an exploded view of the intravenous cannula assembly shown in FIG. 2.

FIG. 4 is a partial longitudinal section view of an intravenous cannula assembly of the present invention wherein the needle blunting apparatus is in its proximally retracted "non-blunting" position.

FIG. 5 is a partial longitudinal view of an intravenous cannula assembly of the present invention wherein the needle blunting apparatus is in its distally advanced "blunting" position.

FIGS. 6, 7 and 8 are a step-wise illustration of a preferred method of using the intravenous cannula assembly of the present invention.

DETAILED DESCRIPTION OF THE PREFERRED EMBODIMENTS

The following detailed description and the accompanying drawings are provided for the purpose of describing and illustrating presently preferred embodiments of the invention only, and are not intended to limit the scope of the invention in any way.

With reference to the drawings, there is shown an over-the-needle intravenous cannula assembly 10 comprising a pliable intravenous cannula 12, a needle 14 and a needle blunting apparatus 16.

The intravenous cannula 12 of the assembly 10 comprises an elongate pliable tubular sheath 18 having a distal taper 20 and a hollow lumen 22 extending longitudinally therethrough. A Luer hub 24 is formed on the proximal end of the elongate pliable sheath 18, as shown.

The needle 14 of the assembly 10 comprises a rigid, elongate needle member 26 having a beveled or otherwise sharpened distal tip 28 and a hollow needle lumen 30 extending longitudinally therethrough. A transparent or partially transparent flash chamber 32 is mounted on the proximal end of the needle member 26. A hollow flash chamber bore 34 extends longitudinally through the flash chamber 32 and leads directly into the hollow lumen 30 of the needle member 26. A cylindrical distal sleeve portion 38, a tapered distal seating member 36 and an annular shoulder 39 are formed on the distal aspect of the flash chamber 32, as shown.

The needle blunting apparatus 16 of the present invention comprises an elongate rigid blunting member 40 formed of material such as stainless steel hypotubing. This rigid blunting member 40 has an outer diameter which is slightly smaller than the inner diameter of the needle member 26. This elongate rigid blunting member 40 has an opening formed in its blunt distal tip 42 and a hollow lumen which extends longitudinally therethrough from the opening in the blunt distal tip to a plurality of proximal outlet apertures 48 formed in the sidewall of the blunting member 40, near its proximal end.

A unidirectional positioning member 44 is mounted on the proximal end of the elongate rigid tube 40. Such unidirectional positioning member 44 is a generally cylindrical body having a series of annular, elastomeric engagement fins 46 formed thereon. These engagement fins 46 are spaced apart and formed in a longitudinal array, as shown. A proximal end surface 50 is formed on the proximal end of the positioning member 44.

FIGS. 4 and 5 show the manner in which the blunting apparatus 16 is inserted through the needle 14 of the assembly 10 to prevent the occurrence of inadvertent skin puncture or other trauma by the beveled or sharpened distal tip 28 of the needle 14. With specific reference to FIG. 4, the blunting apparatus 16 is initially positioned in a first "non-blunting" position wherein only the distal-most ones of the engagement fins 46 are advanced into the proximal portion of the flash chamber bore 34, such that those distal-most ones of the engagement fins 46 are in abutment with, and are proximally deflected by, the surrounding inner wall 45 of the flash chamber bore 34, as shown. When so positioned in its first non-blunting position, blunt distal tip 42 of the blunting member 40 resides within the lumen 30 of the needle 26, at a spaced distance $X_1$ proximal to the sharpened distal needle tip 28.

With reference to FIG. 5, when it is desired to advance the blunting apparatus 16 to its second "blunting" position, distally directed finger pressure may be applied against the proximal surface 50 of the proximal positioning member 44, thereby pushing the blunting apparatus 16 further through the lumen 30 of the needle, to a second position wherein the blunt distal tip 42 of the blunting member 40 extends out of and slightly beyond the sharpened distal needle tip 28, thereby preventing the sharpened distal needle tip 28 from causing penetration trauma. When so advanced to its second "blunting" position, the proximal positioning member 44 is further advanced into the flash chamber bore 34, causing additional ones of the engagement fins 46 to be advanced into the bore 34 and to come into abutment with, and to be proximally deflected by, the surrounding inner wall 45 of the bore 34. Such frictional engagement and proximal deflection of the engagement fins 46 by the inner wall 45 of the bore 34 substantially deters or prevents the blunting apparatus 16 from moving or being retracted in the proximal direction. Such deterrence against subsequent proximal retraction of the blunting member 16 ensures that the blunting member 16 will remain in its second "blunting" position, after the needle member 14 has been removed and discarded.

Preferred Mode of Operation

FIGS. 6a–6c show, in step wise fashion, a preferred method of utilizing the intravenous cannula assembly 10 shown in FIGS. 1–5.

As shown, the protective sheath 11 is initially removed from the intravenous cannula assembly 10, and the blunting apparatus 16 is deployed in its initial or "first" position as shown in FIG. 4. With the blunting apparatus 16 in such first position, the blunt distal tip 42 of the elongate blunting member 40 of the blunting apparatus 16 is retracted within the lumen 30 of the needle member 26 a spaced distance $X_1$ from the sharpened distal tip 28 of the needle member 26. This allows the sharpened distal tip 28 of the needle member 26 to be introduced percutaneously into a blood vessel BV. The introduction of the needle member 26 into the blood vessel BV is verified by the backflow of blood through the lumen 30 of the needle member 26 and the lumen of the blunting member 40 into the flash chamber 32 via the outlet apertures 48 within the blunting member 40. After the distal tip of the needle 26 has been inserted into the blood vessel BV, the needle 14 and the accompanying blunting apparatus 16 (positioned in its "blunting" position) are retracted in the proximal direction, and thumb pressure is applied to the proximal surface 50 of the positioning member 44 of the blunting apparatus 16, thereby forcing the blunting apparatus 16 to move from its first position (FIG. 4) to its second position (FIG. 5) simultaneously with proximal retraction and withdrawal of the needle 14, as shown in FIG. 6b. When in its second position, the distal tip 42 of the blunting member 40 is spaced a distance X2 distally beyond the distal tip 28 of the needle member 26.

Thus, upon its withdrawal, the sharp distal tip 28 of the rigid needle member 26 is effectively blunted or shielded by the blunt distal tip 42 of the elongate blunting member 40 so as to prevent or deter health care workers, trash carriers or others from suffering inadvertent trauma by the sharpened distal tip 28 of the rigid needle member 26.

After the needle 14 and blunting apparatus 16 have been discarded, a solution administration tube SAT having a Luer connector LC thereon is attached to the Luer hub 24 of the intravenous cannula 12 to accomplish fluid infusion through the pliable tubular cannula 18 of the intravenous cannula apparatus 12.

It will be appreciated by those skilled in the art that the invention has been described hereabove with reference to certain presently preferred embodiments only and no effort has been made to exhaustively describe all possible embodiments in which the invention may be practiced. Indeed, those skilled in the art will recognize that various addition, deletions and modifications may be made to the above-described embodiments without departing from the intended spirit and scope of the invention. Accordingly, it is intended that all such additions, deletions and modifications be included within the scope of the following claims.

What is claimed is:

1. A needle assembly comprising:

a tubular needle having a proximal end, a sharpened distal tip, and a lumen extending longitudinally therethrough;

a needle hub attached to the proximal end of the needle and defining a longitudinally extending bore which fluidly communicates with the lumen of the needle;

a blunting member having a proximal end and a blunt distal end, the blunting member being movable relative to the needle from a non-blunting position whereat the distal end is located within the lumen at a prescribed distance proximal to the distal tip, to a blunting position whereat the distal end protrudes from the distal tip; and a positioning member attached to the blunting member and comprising:

a body attached to the proximal end of the blunting member; and a series of pliable engagement fins extending outwardly from the body in spaced relation to each other and sized relative to the bore so as to be proximally deflected when distally advanced into the bore thereby frictionally engaging the needle hub;

the engagement fins being initially advancable into the bore to a first position whereat at least some of the engagement fins frictionally engage the needle hub to maintain the blunting member in the non-blunting position, and thereafter further advanceable into the bore to a second position whereat additional ones of the engagement fins frictionally engage the needle hub to maintain the blunting member in the blunting position;

the frictional engagement of the engagement fins to the needle hub being operable to deter proximal movement of the blunting member subsequent to its distal advancement to the blunting position thereby minimizing the risk of inadvertant penetration trauma caused by the distal tip of the needle.

2. The needle assembly of claim 1 wherein:

the bore of the needle hub has a generally circular cross-sectional configuration and is of a first diameter;

the body of the positioning member has a generally cylindrical configuration; and each of the engagement fins extends radially outward from the body and is of a second diameter which exceeds the first diameter of the bore.

3. The needle assembly of claim 1 wherein:

the blunting member includes a blood inlet opening formed in the distal end thereof, at least one blood outlet opening formed therein in close proximity to the proximal end thereof, and a lumen extending longitudinally therethrough between the blood inlet and outlet openings; and the needle hub is fabricated from a material which is at least partially transparent, and includes a flash chamber which is defined by a distal portion of the bore;

the blood outflow opening being disposed within the flash chamber when the blunting member is in the non-blunting position such that the advancement of the distal tip of the needle into a blood vessel results in the flow of blood proximally through the lumen of the needle, into the blood inlet opening, through the lumen of the blunting member, and out through the blood outlet opening into the flash chamber.

4. The needle assembly of claim 3 wherein the blunting member includes multiple blood outlet openings formed therein.

5. The needle assembly of claim 1 wherein the body of the positioning member is formed to include an enlarged proximal end for assisting in the distal advancement of the engagement fins into the bore.

* * * * *